US007147171B2

(12) United States Patent
Harada et al.

(10) Patent No.: US 7,147,171 B2
(45) Date of Patent: Dec. 12, 2006

(54) DIFFUSER FOR VOLATILE MATERIAL SUCH AS AROMATIC OR CHEMICAL AGENT

(75) Inventors: Shiro Harada, Koga (JP); Masahiko Fujita, Koga (JP)

(73) Assignee: Lumica Corporation, Koga (JP)

( * ) Notice: Subject to any disclaimer, the term of this patent is extended or adjusted under 35 U.S.C. 154(b) by 0 days.

(21) Appl. No.: 11/305,225

(22) Filed: Dec. 19, 2005

(65) Prior Publication Data

US 2006/0157578 A1 Jul. 20, 2006

Related U.S. Application Data

(62) Division of application No. 10/315,240, filed on Dec. 10, 2002, now Pat. No. 7,048,203.

(51) Int. Cl.
*A61L 9/04* (2006.01)
*A61L 9/00* (2006.01)

(52) U.S. Cl. ............... 239/36; 239/44; 239/47; 239/51.5; 239/57; 428/905; 401/132

(58) Field of Classification Search ............... 239/36, 239/44, 47, 51.5, 55–57, 34, 37, 43, 54, 289; 428/905, 74; 401/132, 133, 134; 261/DIG. 88; 128/231.21
See application file for complete search history.

(56) References Cited

U.S. PATENT DOCUMENTS

| | | | |
|---|---|---|---|
| 2,395,109 A | 2/1946 | Fonda | |
| 2,733,098 A | 1/1956 | Holt | |
| 3,614,245 A | 10/1971 | Schwartzman | |
| 3,856,142 A | 12/1974 | Vessalo | |
| 4,058,425 A | 11/1977 | Thrun | |
| 4,275,820 A | 6/1981 | LeBlond | |
| 4,345,716 A | 8/1982 | Armstrong et al. | |
| D272,421 S * | 1/1984 | Sandel | D10/71 |
| 4,609,245 A * | 9/1986 | Sakschek | 239/36 |
| 5,133,458 A | 7/1992 | Miller | |
| 6,039,488 A | 3/2000 | Krawczyk et al. | |
| 6,056,737 A | 5/2000 | Rosen | |
| 6,668,482 B1 * | 12/2003 | Ruffin et al. | 43/42.06 |
| 2002/0109013 A1 | 8/2002 | Desrosiers | |

* cited by examiner

*Primary Examiner*—Kevin Shaver
*Assistant Examiner*—Darren Gorman
(74) *Attorney, Agent, or Firm*—Westerman, Hattori, Daniels & Adrian, LLP

(57) ABSTRACT

There is provided a diffuser for volatile material such as a volatile aromatic or chemical agent. The diffuser has a flexible casing having one or more vent holes formed therein and a breakable glass capsule hermetically enclosing a volatile agent. The capsule is contained in the flexible casing. A liquid-absorbent member is adapted to hold the volatile liquid.

5 Claims, 5 Drawing Sheets

DIFFUSER FOR VOLATILE MATERIAL SUCH AS AROMATIC OR CHEMICAL AGENT

This application is a divisional application of prior application Ser. No. 10/315,240 filed Dec. 10, 2002, now U.S. Pat. No. 7,048,203.

FIELD OF THE INVENTION

The present invention relates to a compact diffuser for volatile material, such as a volatile aromatic or chemical agent, capable of diffusing aroma or chemicals into a surrounding air with simple handling. The volatile aromatic agent is prepared by dissolving a blended aromatic substance of a natural animal- or vegetable-based aromatic substance and a synthetic aromatic substance in alcohol. Aromatic ratio, i.e., aromatic substances to alcohol ratio, is generally 15 to 25%. Cologne usually has aromatic ratio of 2 to 7%. Chemical agents are pesticides, mothproofing agents, insect repellants, etc.

BACKGROUND OF THE INVENTION

A conventional diffuser for volatile material, such as a volatile aromatic or chemical agent has a vapor-permeable casing made of ethylene-vinyl acetate (EVA) resin, and a volatile material such as a volatile aromatic or chemical liquid is enclosed in the inner space of the casing. This diffuser diffuses the volatile constituent of the agent into a surrounding air through the casing by taking advantage of vapor permeability derived from the molecular structure of EVA. It takes several hours to allow the volatile constituent to be diffused into the surrounding air through the EVA resin casing. This slow response is defective from the viewpoint of practicability. In addition, the casing undesirably deforms due to the reduced volume of the liquid caused by the volatilization of the volatile constituent, resulting in deteriorated appearance.

SUMMARY OF THE INVENTION

In view of the above problems, it is therefore an object of the present invention to provide a compact diffuser for volatile material such as a volatile aromatic or chemical agent, capable of promptly diffusing the volatile constituent of the liquid into a surrounding air in a simple operation as the need arises. It is another object of the present invention to provide a diffuser for volatile material, capable of preventing any needless volatilization of the liquid with a simple structure even during a long-term storage.

In order to achieve the above objects, according to the present invention, there are provided:

(1) a diffuser for volatile material such as a volatile aromatic or chemical agent, comprising: a flexible casing having one or more vent holes formed therein; a breakable glass capsule hermetically enclosing a volatile agent, said capsule being contained in the flexible casing; and a liquid-absorbent member adapted to hold the volatile liquid;

(2) a diffuser for volatile material, comprising a flexible casing adapted for detachably attaching the member to an ornamental article, such as an earring, finger ring, wristband, necklace and pendant;

(3) a diffuser for volatile material, comprising a flexible casing adapted for detachably attaching to a writing instrument;

(4) a diffuser for volatile material comprising a flexible casing formed in a configuration usable as an ornamental article such as an earring, finger ring, wristband, necklace and pendant;

(5) a diffuser for volatile material, comprising a cover member with a vent hole, said cover member being provided with an engagement device such as a hook, a pin, and a clip, wherein the cover member is adapted for removably holding the flexible casing therein;

(6) a diffuser for volatile material, for use in a car or in a bathroom, comprising a cover member with a vent hole, which is provided with an engagement device such as a suction cup and a non-slip device, for detachably attaching the cover member, wherein the cover member is adapted for removably holding the flexible casing therein; and (7) a diffuser for volatile material, comprising a flexible casing which can be detachably attached to an ornamental article attached to a string of a portable phone.

The diffuser comprises a flexible casing, which is made of flexible material such as polypropylene resin, polyethylene resin, nylon resin, or vinyl chloride resin, and may be or may not be transparent, opaque or colored.

While FIG. 1 shows a flexible casing formed in a cylindrical shape, any suitable shape may be used according to intended purposes. The flexible casing may have one vent hole, as shown in FIG. 1, or multiple holes on its surface.

The number and/or dimension of the vent holes may be selectively determined in consideration of the volatilization speed of the volatile constituent of the aromatic or chemical liquid to be varied according to intended purposes. Further, in view of volatilization speed to be varied according to the property of the volatile aromatic or chemical liquid, an appropriate holding agent is added into the volatile aromatic or chemical agent to provide a constant volatilization speed for maintaining the diffusion effect for an intended time-period.

The volatile chemical is typically insecticide, mothproofing agent and insect repellent. The insecticide includes, but not limited to, pyrethroid represented by synthetic pyrethrin and pyrethrum. The pyrethroid may also include allethrin, phthalthrin and resmethrin. The mothproofing agent or insect repellent includes, but not limited to, dimethyl phthalate ester, 2-ethyl-1,3-hexane-diol, dimethyl cis-bicyclo<2,2,1>-5-heptene-2,3-dicarboxylate, and N,N-diethyl succinamic acid N-propyl ester.

The mothproofing agent also includes mothproofing agent for fabrics. The volatile aromatic liquid is used as a volatile substance such as perfume or cologne capable of emitting a pleasant or comfortable odor. The capsule is made of thin material such as glass which allows a user to break it with his/her hand. The thickness of the glass capsule may be set, for example, in the range of 0.1 to 0.4 mm.

The capsule made of the vapor-impermeable material such as glass makes it possible to assure a stable quality of the volatile material even during a long-term storage under high-temperature and humid conditions.

The liquid-absorbent member is made of vapor-permeable/liquid-absorbent material such as a natural or synthetic fibrous material, or a natural or synthetic porous material and temporarily holds the liquid of the volatile material.

The liquid-absorbent member may be disposed adjacent to the vent hole as shown in FIG. 1, or wound around the capsule.

When the capsule is broken, the liquid-absorbent member can prevent the resulting outflow of said volatile material from draining from the inner space directly to outside through the vent hole.

Further, the liquid-absorbent member can also prevent such fragments from going out through the vent hole when the capsule is broken into pieces.

REFERENCE NUMERALS

1: Cylindrical Flexible Casing; 2: Glass Capsule; 3: Volatile Material;
4: Liquid-Absorbent Member; 5: Vent Hole; 6: Vent Hole on Outer Wall;
7: Cover Member

PREFERRED EMBODIMENT OF THE INVENTION

The cylindrical flexible casing has a length of 20 to 200 mm, an outer diameter of 3 to 12 mm, and a thickness of 0.2 to 3 mm. A vent hole is formed on an end or both ends of the flexible casing. The flexible casing contains a liquid-absorbent member in inner space.

The glass capsule has an elongated shape along the casing and the closed end of the capsule has a cuspidate shape. The volatile material preferably is hermetically enclosed into the capsule through a process of preparing a cylindrical elongate ample having a planar opening, introducing the volatile material into the capsule through the planar opening, and thermally melting and closing the opening without delay. The process, however, is not limited to this particular process.

When a user bends the flexible casing by his/her hand to break the capsule. This breaking operation is facilitated by virtue of the cylindrical elongated shape of the flexible casing. Upon the breakage of the capsule, the volatile liquid is temporarily held by the liquid-absorbent member, and gradually volatilized and diffused from the liquid-absorbent to the surrounding air through the vent hole.

With reference to the accompanying drawings, various embodiments of the present invention will now be described.

Figure 1:
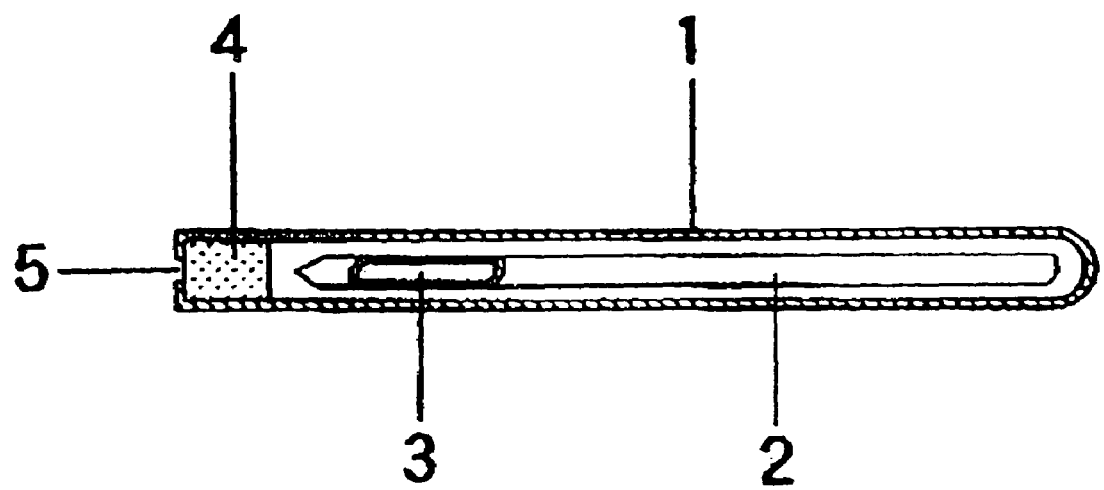
FIG. 1 is an explanatory sectional view of a diffuser for volatile material according to a first embodiment of the present invention.

FIG. 1 is an explanatory sectional view of a diffuser for volatile material according to a first embodiment of the present invention.

Figure 2:
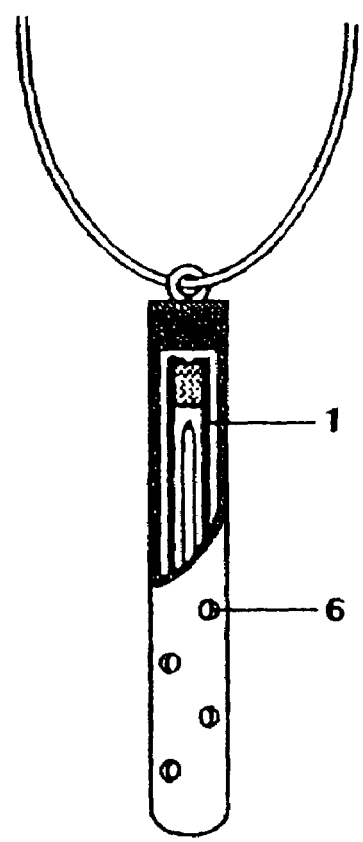
FIG. 2 is an explanatory view of a pendant type diffuser according to a second embodiment of the present invention.

FIG. 2 is an explanatory view of a pendant type diffuser according to a second embodiment of the present invention. The diffuser includes a cylindrical cover member made of metal or plastic material and formed with a plurality of vent holes.

Figure 3:
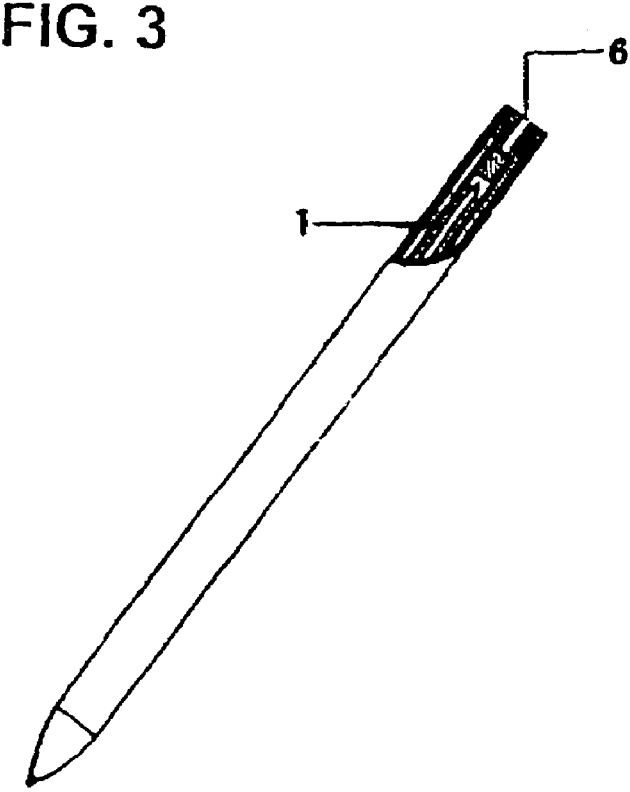
FIG. 3 is an explanatory view of a pencil type diffuser according to a third embodiment of the present invention.

FIG. 3 is an explanatory view of a pencil type diffuser according to a third embodiment of the present invention. The diffuser includes a cover member formed as a pencil. The cover member has a receiving space for receiving the flexible casing, and a cap formed with a vent hole.

Figure 4:
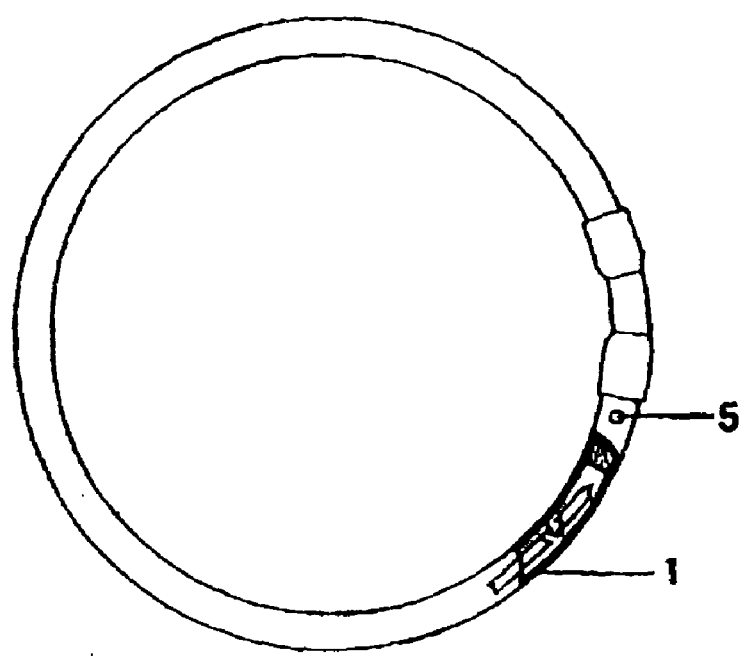
FIG. 4 is an explanatory view of a wristband type diffuser according to a fourth embodiment of the present invention.

FIG. 4 is an explanatory view of a wristband type diffuser according to a fourth embodiment of the present invention. In this embodiment, the diffuser includes a pipe-shaped polyethylene-resin flexible casing having an outer diameter of 5 mm and a length of 180 mm, and a joint for coupling both ends of the flexible casing. The flexible casing contains the liquid-impermeable/breakable capsule enclosing a volatile aromatic liquid, and the liquid-absorbent member as in the first embodiment. A vent hole is formed at one end of the flexible casing and covered by the liquid-absorbent member. When diffuser is used, the flexible casing is bent to break the capsule, and both ends of the flexible casing are coupled by the joint to use as a wristband. This diffuser may be soled as a combinatorial ornament of the joint and the flexible casing with the capsule and the liquid-absorbent member.

Figure 5:
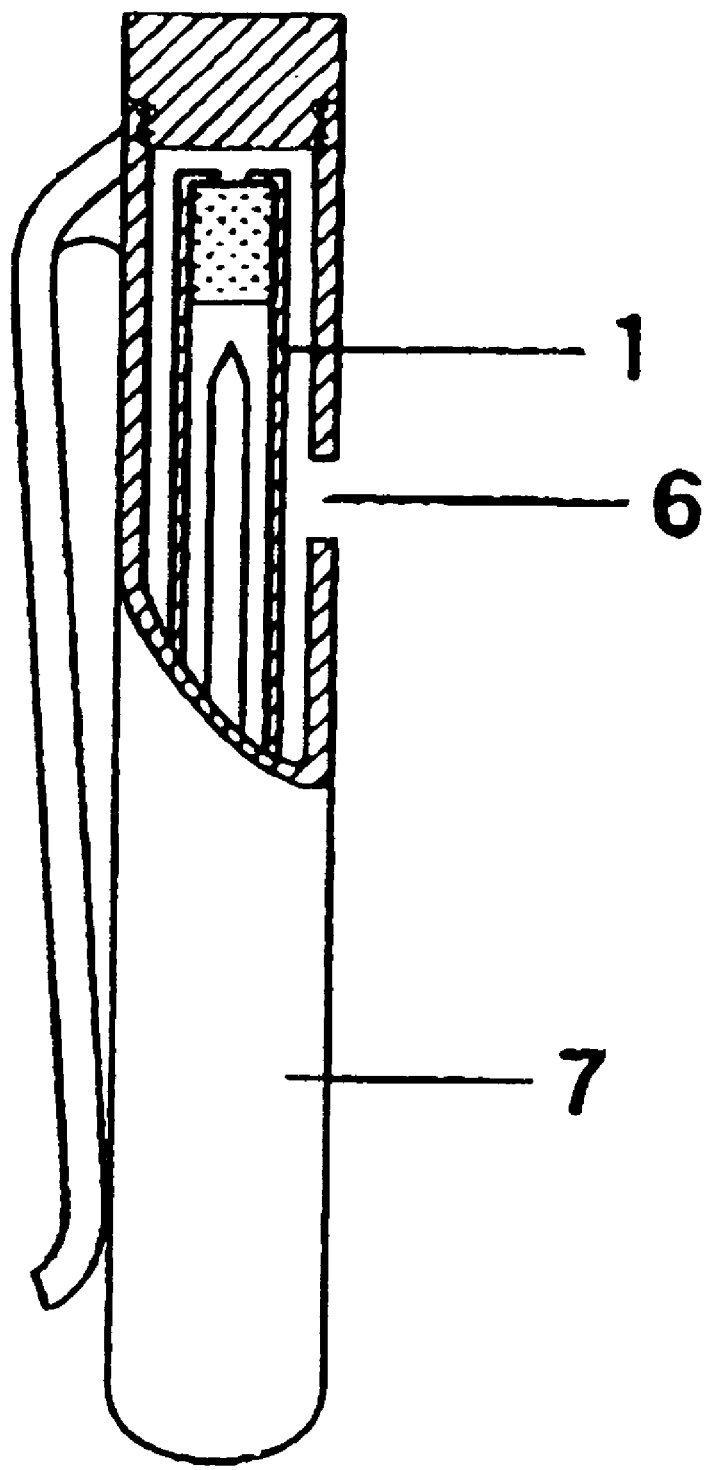
FIG. 5 is an explanatory view of a mothproofing diffuser according to a fifth embodiment of the present invention.

FIG. 5 is an explanatory view of a mothproofing diffuser according to a fifth embodiment of the present invention. In this embodiment, the diffuser includes a cover member having a receiving space, a vent hole, and a detachable cap, and a clip provided on the opposite side of the vent hole. The flexible casing to be received in the receiving space contains the liquid-impermeable/breakable capsule enclosing a volatile mothproofing agent, and the liquid-absorbent member.

Figure 6:
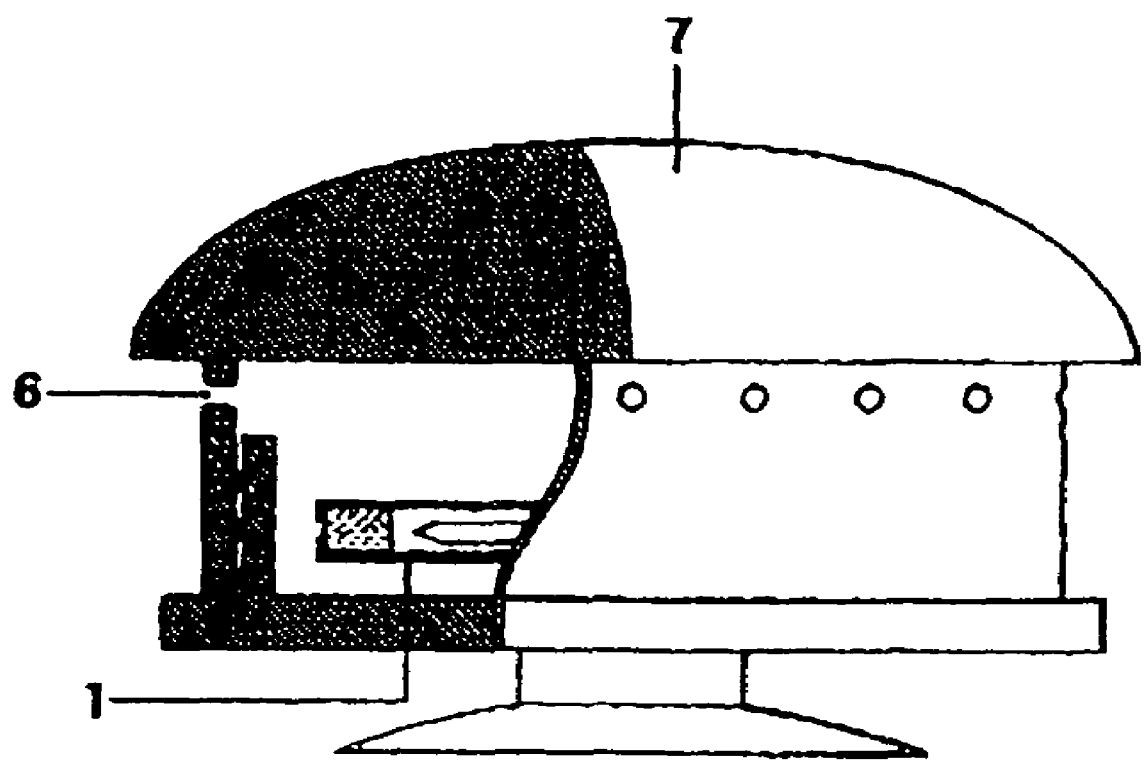
FIG. 6 is an explanatory view of an aroma diffuser for use in a bathroom according to a sixth embodiment of the present invention.

FIG. 6 is an explanatory view of an aroma diffuser for use in a bathroom according to a sixth embodiment of the present invention. In this embodiment, the diffuser includes a cover member having a receiving space, a plurality of vent holes, and a detachable cap, and a suction cup provided on the opposite side of the cap.

Figure 7:
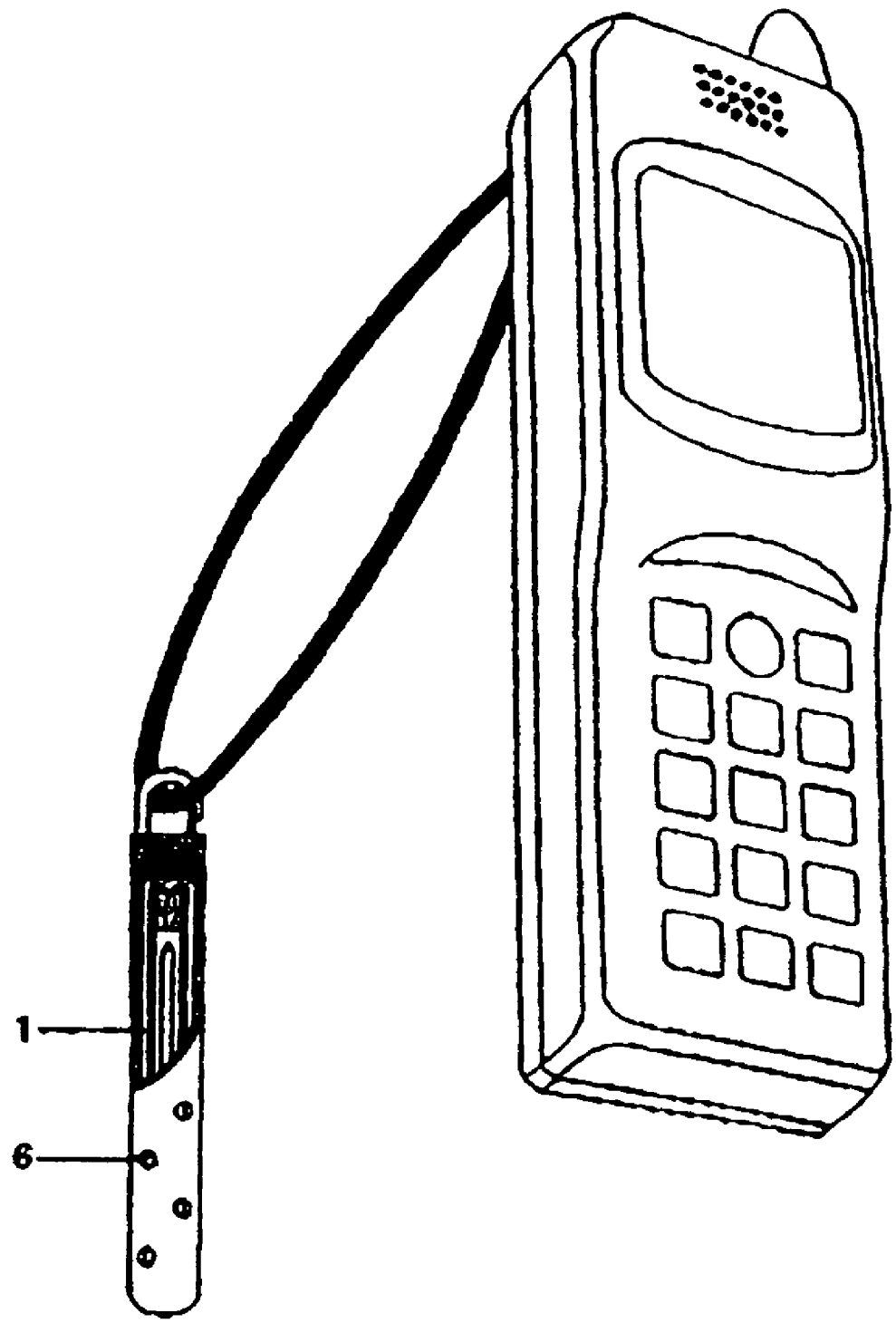
FIG. 7 is an explanatory view of an ornamental diffuser used with a portable phone according to a seventh embodiment of the present invention.

FIG. 7 is an explanatory view of an ornamental diffuser used with a portable phone according to a seventh embodiment of the present invention. The diffuser can be detachably attached to a string of a portable phone through the hook.

As described above, the present invention can provide a compact diffuser capable of promptly diffusing the volatile constituent of the liquid into a surrounding air in a simple operation as the need arises while maintaining a stable volatilization of the liquid with extended effective life. The present invention also allows the diffuser to be stored for a long term without deterioration in quality. In addition, the present invention provides venous ornamental or practical applications to the diffuser. Further, the diffuser can be flexibly used according to intended purposes by preparing a plurality of capsules enclosing different kinds of volatile aromatic or chemical liquids.

What is claimed is:

1. A diffuser for volatile material, comprising:
   a housing;
   a flexible casing provided in the housing, the flexible casing having a cylindrical shape with an opened end and a closed end;
   a breakable glass capsule provided in the flexible casing;
   a volatile agent hermetically enclosed in the breakable glass capsule, the volatile agent including an aromatic agent or chemical agent; and
   an absorbent member provided right inside the opened end of the flexible casing, wherein the absorbent member is not projected outside the opened end.

2. A diffuser for volatile material according to claim 1, wherein the housing has a hook to be engaged in an ornamental article.

3. A diffuser for volatile material according to claim 1, wherein the housing is designed to be adapted into a writing instrument.

4. A diffuser or volatile material according to claim 1, wherein the housing has an engagement to be adapted into a string of a portable phone.

5. A diffuser or volatile material according to claim 1, wherein the absorbent member is disposed inside and adjacent to the opened end without being wound around the breakable glass capsule, wherein the opened end has an opening smaller than an inner diameter of the flexible casing.

* * * * *